United States Patent [19]
Schlaeppi et al.

[11] Patent Number: 5,516,938
[45] Date of Patent: May 14, 1996

[54] IMMUNOLOGICAL DETECTION METHOD

[75] Inventors: Jean-Marc Schlaeppi, Basle, Switzerland; Dietmar Hüglin, Freiburg, Germany

[73] Assignee: Ciba-Geigy Corporation, Ardsley, N.Y.

[21] Appl. No.: 369,241

[22] Filed: Jan. 6, 1995

Related U.S. Application Data

[62] Division of Ser. No. 988,509, Dec. 10, 1992, abandoned.

[30] Foreign Application Priority Data

Dec. 12, 1991 [CH] Switzerland ............... 3652/91

[51] Int. Cl.$^6$ ................................. C07C 311/51
[52] U.S. Cl. ................................. 562/430; 564/91
[58] Field of Search ............... 562/430; 564/91

[56] References Cited

FOREIGN PATENT DOCUMENTS

| | | |
|---|---|---|
| 1223589 | 6/1987 | Canada . |
| 0120814 | 10/1984 | European Pat. Off. . |
| 0463998 | 1/1992 | European Pat. Off. . |
| WO91/04967 | 4/1991 | WIPO . |

OTHER PUBLICATIONS

Ahmad, I., et al., "Trace Residue Analysis of the Herbicide Chlorsulfuron in Soil by Gas Chromatography–Electron Capture Detection", *J. Agric. Food Chem.*, 38:138–141 (1990).
Campbell, A. M., *"Monoclonal Antibody Technology"*, in: Laboratory Techniques in Biochemistry and Molecular Biology: Burden, Knippenberg (Eds.); Elsevier, Amsterdam; vol. 13, pp. 120–184 (1984).
De Luca, "Immunoflourescence Analysis"; in *Antibody As a Tool*, Marchalonis et al., John Wiley & Sons, Ltd., pp. 1890231 (1982).
Ercegovich, C. D., et al., "Develoment of a Radioimmunoassay for Parathion", *J. Agric. Food Chem.*, 29:559–563 (1981).
Feng, P. C. C., et al., "Development of an Emzyme–linked Immunosorbent Assay for Alachlor and Its Application to the Analysis of Environmental Water Samples", *J. Agric. Food Chem.*, 38:159–163 (1990).
Fleeker, J., "Two Enzyme Immunoassays to Screen for 2,4–Dichlorophenoxyacetic Acid Water", *J. Assoc. Off. Anal. Chem.*, 70(5):874–878 (1987).
Hargrove, R. S., et al., "The Loss of Alachlor from Soil", *Weed Sci.*, 19(6):652–654 (1971).

Iwanzik, W., et al., "Biotest zur Bestimmung von Trlasulfuron im Boden", *Z. PflKrankh. PflSchutz*, Suppl. XI:301–310 (1988).
Kawamura, H., et al., "Enhancement of Antigenic Potency in Vitro and Immunogenicity in Vivo by Coupling the Antigen to Anti–Immunoglobulin", *J. Immunol.*, 136(1):58–65 (1986).
Kelley, M. M., et al., "Chlorsulfuron Determination in Soil Extracts by Enzyme Immunoassay", *J. Agric. Food Chem.*, 33:962–965 (1985).
Köhler, G., et al., "Continuous Cultures of Fused Cells Secreting Antibody of Predefined Specificity", *Nature*, 256:495–497 (1975).
Kulkarni, P. N., et al., "Covalent Binding of Methotrexate to Immunoglobulins and the Effect of Antibody–linked Drug on Tumor Growth in Vivo", *Cancer Res.*, 41:2700–2706 (1981).
Littlefield, J. W., "Selections of Hybrids from Matings of Fibrolbasts in vitro and Their Presumed Recombinants", *Science*, 145:709–710 (1964).

*Primary Examiner*—José G. Dees
*Assistant Examiner*—Samuel Barts
*Attorney, Agent, or Firm*—Andrea C. Walsh; W. Murray Spruill

[57] ABSTRACT

The present invention relates to monoclonal antibodies that are distinguished by a high degree of selectivity and affinity towards herbicides from the group of the sulfonylureas, especially towards sulfonylurea herbicides of formula (A)

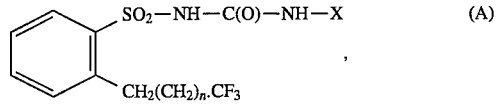

wherein

X is a mono- or di-substituted 6-membered heterocycle having from one to three nitrogen atoms and bonded via carbon, but is preferably mono- or di-substituted s-triazine or pyrimidine; and n is an integer from 0 to 4, preferably the number 1, and that are therefore outstandingly suitable for use in an immunoassay for the rapid and effective detection of the said sulfonylurea herbicides in soil, water or air samples or in plant extracts, and to methods for the production of said monoclonal antibodies.

The present invention relates also to hybridoma cell lines that produce said monoclonal antibodies and to immunological detection methods using said monoclonal antibodies, and to test kits that may be used in those detection methods.

6 Claims, No Drawings

IMMUNOLOGICAL DETECTION METHOD

This is a Divisional Application of Ser. No. 07/988,509 filed Dec. 10, 1992 now abandoned.

The present invention relates to monoclonal antibodies that are distinguished by a high degree of selectivity and affinity towards herbicides from the group of the sulfonylureas, especially towards sulfonylurea herbicides of formula (A)

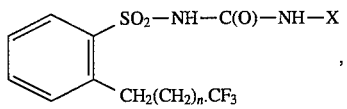

wherein

X is a mono- or di-substituted 6-membered heterocycle having from one to three nitrogen atoms and bonded via carbon, but is preferably mono- or di-substituted s-triazine or pyrimidine; and n is an integer from 0 to 4, preferably the number 1, and that are therefore outstandingly suitable for use in an immunoassay for the rapid and effective detection of the said sulfonylurea herbicides in soil, water or air samples or in plant extracts, and to methods for the production of said monoclonal antibodies.

The present invention relates especially to monoclonal antibodies that are distinguished by a high degree of selectivity and affinity towards compounds of formula (I)

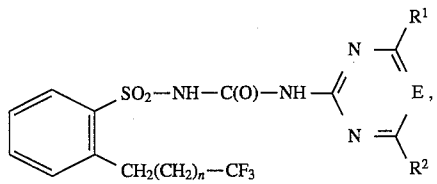

wherein $R^1$ and $R^2$ are each independently of the other hydrogen, halogen, $C_1$–$C_4$alkyl, $C_1$–$C_4$haloalkyl, $C_2$–$C_4$haloalkoxy, $C_1$–$C_4$alkylthio, $C_1$–$C_4$haloalkylthio, $C_2$–$C_4$alkoxyalkyl, methoxy, ethoxy or —$NR^3R^4$, wherein $R^3$ and $R^4$ are each independently of the other hydrogen or $C_1$–$C_4$alkyl;

E is nitrogen or a methine bridge; and n is an integer from 0 to 4, preferably 1.

In the above definitions, alkyl is to be understood as being straight-chain or branched alkyl, such as methyl, ethyl, n-propyl, isopropyl and the four isomeric butyl radicals. Methyl and ethyl are preferred.

Alkoxy is to be understood as being: methoxy, ethoxy, n-propoxy, isopropoxy, and the four isomeric butoxy radicals, but especially methoxy, ethoxy and isopropoxy.

Examples of alkylthio are methylthio, ethylthio, n-propylthio, isopropylthio and n-butylthio, but especially methylthio and ethylthio.

Halogen, irrespective of whether it appears on its own or as a constituent of a haloalkyl, haloalkoxy or haloalkylthio group, is to be understood as being fluorine, chlorine and bromine, preferably fluorine and chlorine. Examples of haloalkyl are chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 1,1,2,3,3,3-hexafluoropropyl, but especially fluoromethyl, chloromethyl, difluoromethyl and trio fluoromethyl.

Special preference is given to monoclonal antibodies that are distinguished by a high degree of selectivity and affinity towards a compound of the following formula (II)

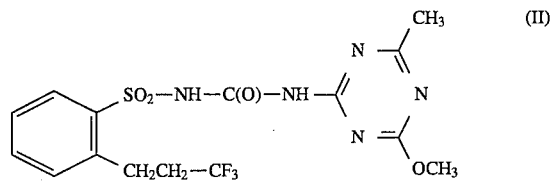

and that are therefore outstandingly suitable for use in an immunoassay for the rapid and effective detection of the said sulfonylurea herbicide according to formula (II) in soil, water or air samples or in plant extracts, and to methods for the production of said monoclonal antibodies.

The present invention relates further to hybridoma cell lines that produce said monoclonal antibodies and to immunological methods for the detection of sulfonylurea herbicides of formula (A) in soil, water or air samples and in biological material, for example plant extracts, using said monoclonal antibodies, and to the test kits that may be used in those detection methods.

Sulfonylureas are a new class of especially effective herbicides that are used for plant protection purposes, especially for the selective and effective control of broad-leaved weeds in cereal crops.

A representative of that class is the above-mentioned compound of formula (II), an N-[2-(3,3,3-trifluoropropyl)-phenylsulfonyl]-N'-(4-methoxy-6-methyl-1,3,5-triazin-2-yl)urea, which is used especially in maize crops for the selective control of broad-leaved weeds, such as *Amaranthus retroflexus* or *Chenopodium album*.

The detection of herbicides from the group of the sulfonylureas in soil and water samples is at present carried out mainly by means of gas or liquid chromatography (for example HPLC) [GC: Ahmad and Crawford (1990); HPLC: Zahnow (1982); Iwanzik and Egli (1988); van Rensburg E (1985)] and using bioassays.

Since in some cases even very small residues of those herbicides in the soil still exhibit a high degree of residual activity, which may be harmful especially to subsequent crops that are susceptible to sulfonylureas, it is of great importance, especially for the farmer, to have available a reliable and extremely sensitive detection method for residue analysis.

Although most of the methods mentioned above for the detection of synthetic herbicides do have the sensitivity necessary for residue analysis, their use is generally associated with a large number of disadvantages. For example, for the determination of sulfonylurea herbicides in soil samples using GC or HPLC, laborious purifying and concentrating steps have to be effected before the actual chromatographic analysis is carried out. Those methods cannot therefore be carried out under field conditions, as they involve the use of a considerable amount of apparatus.

Other disadvantages of those methods are, for example, that gas chromatography involves the use of detectors that are element-specific only, while HPLC involves the use of photometric detectors, which are relatively non-specific. With the exception of detection by mass spectroscopy, the chromatographic analyses rely on the determination of the retention times for the particular substance. Those values are, however, relative and are therefore not structure-specific.

The bioassay methods that are likewise mentioned above are relatively simple to carry out, but are not sufficiently specific.

In order to avoid the above-described disadvantages of the established analytical methods, attempts have recently been made to develop immunological methods—such as are already used routinely in clinical diagnosis for the detection of a wide variety of antigens—for the agricultural sector also, especially for the quantitative and qualitative determination of agricultural chemicals in soil, water or air samples.

For example, work is already underway on the development of immunological methods for the detection of specific herbicides, such as 2,4-dichlorophenoxyacetic acid (Fleeker, 1986) or chlorosulfurone (Kelley et al, 1985), and of various pesticides, such as difluobenzurone (Wie and Hammock, 1982), metalaxyl (Newsome, 1985), alachlor (Feng et al, 1990) or parathion (Ercegovich et al, 1981).

Methods for the immunological detection of herbicides from the group of the sulfonylureas have thus already been described [Kelly et al (1985)], but they, like the methods described hereinbefore, rely on the use of polyclonal antisera obtained from animals that have previously been immunised with a corresponding antigen. The production of monoclonal antibodies to sulfonylurea herbicides that have a sufficiently high degree of affinity towards the target substance and are therefore suitable for use according to the invention in one of the known immunoassays has not yet been successful, however.

Polyclonal antisera are of very heterogeneous composition, that is to say they comprise a large number of different antibodies that react with different epitopes of the particular antigen. This heterogeneous composition of polyclonal antisera results from the fact that whenever an experimental animal is immunised with a specific antigen, several antibody-producing cell clones are stimulated at the same time; each of those clones recognises a different epitope on the antigen molecule and, as a result, different antibodies are produced by the stimulated cell clones.

For that reason, sera of immunised animals are always polyclonal and therefore heterogeneous, as regards both their specificity and their membership of the individual classes of immunoglobulins.

This heterogeneity of the composition of polyclonal antisera may therefore lead to a situation in which, owing to insufficient affinity, their detection sensitivity is not adequate for the selective detection of a specific target substance, or in which structurally closely related compounds, for example the target substance [compound of formula (II)] and its hydroxylation products, cannot be adequately differentiated when using polyclonal antibodies in the context of an immunoassay.

In order to overcome those disadvantages of the polyclonal antisera, there has recently been an increase in efforts aimed at the development of monoclonal antibodies for the agricultural sector also. For example Schlaeppi et al (1989) report on the production and use of monoclonal antibodies to atrazine and hydroxyatrazine in an enzyme-linked immunoassay.

The problem to be solved within the context of this invention was thus especially to provide an easy to use, effective and highly selective immunoassay for the rapid and reliable detection of sulfonylurea herbicides of formula (A), especially for the detection of sulfonylurea herbicides of formula (I) and more especially for the detection of a compound of the following formula (II)

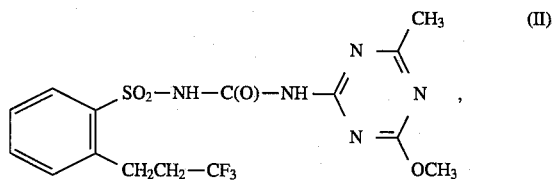

for example in soil, water and air samples.

This problem has now been solved, surprisingly, within the context of the present invention by providing monoclonal antibodies having a high degree of specificity and affinity towards sulfonylurea herbicides of formula (A), but especially towards a compound of formula (II), using the hybridoma/monoclonal antibody technology that is known per se.

The use of hybrid somatic cell lines (hybridomas) as the source for antibodies to quite specific antigens dates back to the work of Köhler and Milstein (*Nature*, 256: 495–497, 1975).

The antibodies that can be obtained by means of the method described therein differ very greatly from those obtained from antisera of conventionally immunised animals.

The principle of hybridoma/monoclonal antibody technology is based on the observation that when two somatic cells fuse, the resulting hybrid cell exhibits characteristic features of both parent types.

In the case of monoclonal antibody production, the ability to synthesise a specific antibody originates from an immunocompetent B cell (usually a spleen cell) taken from a previously immunised donor animal, while the capacity for continuous cell division in culture is supplied by the other fusion partner, a tumour cell line (often a myeloma).

The donor animals are generally immunised using conjugates consisting of the target molecule and a high molecular weight carrier molecule linked thereto.

Each of those hybrid cell lines synthesises a homogeneous immunoglobulin that is only one single representative from the large number of possible antibodies that can be synthesised in vivo by an animal in response to an antigen.

Since each immunoglobulin-producing clone is characterised by a single type of antibody, the expression "monoclonal antibody" has become accepted.

The advantages of monoclonal antibodies over polyclonal antibodies are many:

a) monoclonal antibodies can be obtained in large numbers and in a high degree of purity, b) the production of monoclonal antibodies is homogeneous as regards the antigen reactivity and does not change over time, c) monoclonal-antibody-producing hybridomas can be stored for years or even decades without losing their specific properties, i.e. the production of specific monoclonal antibodies, d) monoclonal antibodies are better suited for use as standard reagents than are polyclonal antisera, since the latter are adversely affected by a large number of variable factors. Those factors include, for example:

α) the removal of blood from immunised animals for the purpose of obtaining antiserum, β) the problem of constant availability of material for additional immunisation, γ) the limited lifespan of the donor animals.

Monoclonal antibodies, which have now been produced to a large number of antigens, are well established especially in medical diagnosis, where their use is now quite indispensable.

Within the context of the present invention, there has now been made available for the first time a monoclonal antibody having a high degree of specificity and affinity towards sulfonylurea herbicides of formula (A), and especially towards a compound of formula (II), that can be produced using the hybridoma/monoclonal antibody technology that is known per se and is outlined briefly above and that is suitable by virtue of its high degree of affinity towards the target substance for use according to the invention in one of the known immunoassays.

In detail, in the production of monoclonal antibodies to sulfonylurea herbicides of formula (A), the procedure is as follows: in the preparation of the immunogen intended for the immunisation there is used a fragment that includes especially the sulfonamide moiety of the molecule, and that fragment is linked to one of the high molecular weight carrier molecules customarily used.

After the immune response has been triggered in the donor animal, the cells responsible for the production of antibodies are isolated from the donor animal and fused with suitable myeloma cells in order to produce hybridoma cells in the manner described in detail below.

The present invention thus relates to a method for the production of a monoclonal antibody having a high degree of specificity and affinity towards one or more sulfonylurea herbicides according to formula (A), wherein (a) a linking component that consists essentially of the sulfonamide moiety of the target molecule is conjugated with a suitable high molecular weight carrier molecule;

(b) a donor animal is immunised with the conjugate prepared in accordance with (a);

(c) immunocompetent B cells are isolated from the immunised donor animal;

(d) the said immunocompetent B cells are fused with tumour cells capable of continuous cell division;

(e) the resulting fusion product is isolated and after selection the hybridoma cells that produce the desired antibody are cloned, and (f) the said hybridoma cells are cultured in vitro or in vivo to produce monoclonal antibodies.

The procedure described above can be used also in the production of monoclonal antibodies to a compound of formula (I), but especially in the production of monoclonal antibodies of formula (II). Alternatively, in this case it is also possible for the whole molecule to serve as the immunogen, provided it is linked via a spacer molecule to one of the high molecular weight carrier molecules customarily used.

The present invention relates also to the monoclonal antibodies obtainable by the method according to the invention. Preferred are monoclonal antibodies having a high degree of specificity and affinity towards sulfonylurea herbicides of formula (A), especially towards sulfonylurea herbicides of formula (I) and more especially towards a compound of formula (II), that are outstandingly suitable, by virtue of their low cross-reactivity with a large number of structurally related compounds, for use in an immunoassay for the rapid and reliable detection of the said sulfonylurea herbicides and that can therefore be used also for differentiating the target substances from structurally related compounds, such as from their hydroxylation products and inactive metabolites.

Special preference is therefore given within the context of the present invention especially to monoclonal antibodies and to the derivatives thereof that have a high degree of specificity and affinity towards a compound of formula (II) and that exhibit essentially no cross-reactivity with a large number of structurally related compounds, such as triasulfurone, primisulfurone and chinosulfurone, and compound A in Table 2.

Special preference is likewise given to monoclonal antibodies that have a high degree of specificity and affinity towards a compound of formula (II) and that exhibit a cross-reactivity of <1.0%, but especially of <0.4%, and most especially of <0.1%, with a large number of structurally related compounds, such as triasulfurone, primisulfurone and chinosulfurone, and compound A in Table 2.

Especially preferred is a monoclonal antibody obtainable from the hybridoma cell line that has the distinguishing characteristics of ECACC 911 20619, as well as derivatives of the said monoclonal antibody.

Within the context of the present invention, derivatives of monoclonal antibodies are to be understood as being, for example, antibody fragments that still have the high degree of specificity and affinity for the antigenic determinants of the sulfonylurea herbicides of formula (A), but especially for the antigenic determinants of a compound of formula (II); radioactively labelled monoclonal antibodies that are labelled, for example, with radioactive iodine ($^{125}I$, $^{131}I$), carbon ($^{14}C$), sulfur ($^{35}S$), tritium ($^{3}H$) or the like; conjugates of monoclonal antibodies with biotin or avidin, with enzymes, such as horseradish peroxidase, alkaline phosphatase, β-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (for example luciferase), chemoluminescent agents (for example acridine esters) or fluorescent agents (for example phycobiliproteins). The present Application likewise includes bispecific and cross-linked antibodies. This list of examples of possible antibody derivatives serves merely to illustrate the present invention and is not intended to limit the subject of the invention in any way.

Within the context of this invention, the expression "essentially no cross-reactivity" is intended to be understood as meaning that the reactivity of the monoclonal antibodies specific to sulfonylurea herbicides of formula (A), but especially to a compound of formula (II), with non-specific epitopes of other compounds, especially structurally related compounds, such as triasulfurone, is in the majority of cases less than 10%, and preferably less than 1.5%, especially less than 0.1%.

As defined within the context of this invention, the percentage of cross-reactivity is represented by the following equation:

[antigen concentration for 50% inhibition ($I_{50}$)/concentration of the antigen analogs for 50% inhibition ($I_{50}$)]×100.

The $I_{50}$ value can be determined, for example, by means of a competitive ELISA assay (see Example 8). In that case, for example, the $I_{50}$ value corresponds to the antigen concentration that results in a 50% inhibition of the binding of the antibody to the carrier-bound antigen.

The present invention relates further to hybridoma cell lines that synthesise and preferably secrete into the surrounding medium the monoclonal antibodies characterised in detail hereinbefore.

The present invention relates especially to a hybridoma cell line that produces a monoclonal antibody that has a high degree of specificity and affinity towards sulfonylurea herbicides of formula (A), especially towards sulfonylurea herbicides of formula (I) and more especially towards a compound of formula (II), and that by virtue of its low cross-reactivity is outstandingly suitable for use in an immunoassay for the rapid and reliable detection of sulfonylurea herbicides of formula (A), especially for the detection of sulfonylurea herbicides of formula (I) and more especially for the detection of a compound of formula (II), and that can therefore be used also for differentiating the target substances from structurally related compounds, for example from their hydroxylation products and inactive metabolites.

Within the context of the present invention, special preference is therefore given to a hybridoma cell line that produces a monoclonal antibody that has a high degree of specificity and affinity towards a compound of formula (II) and that exhibits essentially no cross-reactivity with a large number of structurally related compounds, such as triasulfurone, primisulfurone and chinosulfurone, and compound A in Table 2.

Special preference is likewise given to a hybridoma cell line that produces a monoclonal antibody that has a high degree of specificity and affinity towards a compound of formula (II) and that exhibits a cross-reactivity of <1.0%, especially of <0.4%, and most especially of <0.1%, with a large number of structurally related compounds, such as triasulfurone, primisulfurone and chinosulfurone, and compound A in Table 2.

Very special preference is given to a hybridoma cell line that produces a monoclonal antibody according to the invention and that has the distinguishing characteristics of ECACC 911 20619, and to clones and sub-clones thereof.

The present invention relates also to variants and mutants of the hybridoma cell lines characterised in detail above that occur spontaneously or that can be produced artificially using known methods and that still have the characteristic properties of the starting material, that is to say are still capable of producing the antibodies according to the invention or derivatives thereof and secreting them preferably into the surrounding medium.

The present invention also includes methods for the production of said hybridoma cell lines and to methods for the production of said monoclonal antibodies.

Clones and sub-clones of hybridoma cell lines are to be understood as being hybridomas that are produced from the starting clone by repeated cloning and that still have the features of the starting clone that are essential to the invention.

The invention relates also to a method for the immunological detection of sulfonylurea herbicides of formula (A), especially for the detection of sulfonylurea herbicides of formula (I), and more especially for the detection of a compound of formula (II), for example in soil, water or air samples and in biological material, for example in plant or animal extracts, using the monoclonal antibodies according to the invention.

The present invention also includes means for the qualitative and quantitative determination of sulfonylurea herbicides of formula (A), especially of sulfonylurea herbicides of formula (I), and more especially for the determination of a compound of formula (II), in the form of ready-to-use test kits that comprise at least one of the monoclonal antibodies according to the invention as reagent. Special preference is given to a test kit that is suitable for use under field conditions for the rapid and reliable detection of the mentioned sulfonylurea herbicides.

The monoclonal antibodies according to the invention are produced using methods known per se that are based essentially on the methods developed by Köhler und Milstein (1975).

Since the target substances [sulfonylurea herbicides of formula (A)] to be analysed, for example the compound according to formula (II), for which specific monoclonal antibodies are to be developed, are relatively small and simple molecules which after administration to an experimental animal are not capable alone of triggering a corresponding immune response in that animal, it is necessary to take preparatory measures before the actual immunisation.

Compounds that owing to their size and simple structure are not capable of inducing an immune reaction are called haptens or incomplete antigens and are therefore distinguished from the complete antigens (=immunogens) which act as antigens and are capable of inducing an immune response. Such hapten molecules may be conjugated to high molecular weight compounds (carrier molecules), as a result of which they become comparable to complete antigens as regards their characteristics, that is to say they are then capable of triggering an immune response.

Some of the antibodies formed in the course of the immunisation reaction are then capable of reacting with specific epitopes on the hapten molecule, regardless of whether the hapten molecule is present alone or is still linked to the carrier molecule.

Within the context of this invention, therefore, before experimental animals are immunised, the target substance acting as a hapten is linked to a high molecular weight carrier that is suitable for imparting to the target substance acting as a hapten the activity of a complete antigen.

By suitable carrier molecules there are to be understood within the context of this invention especially macromolecular compounds that have freely accessible reactive groups for the linking reaction with the hapten and that are capable, by being linked to the hapten, of imparting to the latter an immunogenic potential or of reinforcing its existing immunogenicity.

Special preference is given within the context of this invention to macromolecular compounds containing freely accessible reactive amino groups.

Very especially preferred for use according to the invention as carrier molecule are lysine-rich proteins having a molecular weight of from 10 000 to 1 500 000, for example bovine serum albumin (BSA: MW 66 200), human serum albumin (HSA; MW 58 000) or keyhole limpet haemocyanin (KLH; MW>1 000 000), which are commercially available and are thus available in any desired amount.

It is, of course, possible within the context of the present invention also to use other macromolecular compounds as carrier molecules provided that they fulfil the abovementioned requirements, such as porcine thyroglobulin, B2 microglobulin, haemocyanin, immunoglobulins, toxins (cholera, tetanus, diphtheria toxin, etc.), polysaccharides, lipopolysaccharides, natural or synthetic polyadenyl and polyuridyl acids, polyalanine and polylysine polypeptides or cell-membrane components, for example formalin- or glutaraldehyde-treated erythrocyte cell membranes.

Also suitable for use as carrier molecule in the method according to the invention is, for example, the purified rabbit IgG fraction against mouse IgG (H+L) according to the method described by H Kawamura and JA Berzofsky (1986).

The conjugation of the hapten to the carrier molecule can be effected either directly or, preferably, by way of a bridge member which is optionally first added onto the hapten molecule.

The linking of the substance to be analysed to the carrier molecule must be effected in such a manner that the relevant structural elements of the target substances remain freely accessible and are thus capable of triggering a specific immune response, that is to say of inducing the formation of specific antibodies. In the preparation of the sulfonylurea derivatives, especially of derivatives of the compound of formula (II), care must therefore be taken that those structural elements are retained.

That can be achieved, for example, by derivatising a sulfonylurea herbicide of formula (A), especially a compound of formula (II), in a manner that allows it to be linked to one of the above-mentioned carrier molecules without impairing the said relevant structural elements.

Special preference is given in the context of the derivatisation to the use of selected fragments of the molecule instead of the whole intact sulfonylurea molecule. In that way, monoclonal antibodies having a high degree of affinity and selectivity towards sulfonylurea herbicides of formula (A), but especially towards a compound of formula (II), can thus be produced using solely the sulfonamide moiety as linking component, instead of the complex whole molecule consisting of sulfonamide moiety, urea bridge and heterocycle moiety, and linking that sulfonamide moiety, as described hereinbefore, to a suitable carrier molecule. That is of great advantage from a technical point of view, since fragments of the molecule are easier to handle than is the very much more complex whole molecule.

As shown within the context of the present invention, the immunisation of donor animals with the conjugate described hereinbefore, which consists of one of the customarily used high molecular weight carriers and the sulfonamide moiety of a sulfonylurea herbicide according to formula (A), results, surprisingly, in the production of highly specific antibodies.

An important aspect of the present invention is thus the use of the sulfonamide moiety of sulfonylurea herbicides according to formula (A), especially of sulfonylurea herbicides of formula (I), and more especially of a compound of formula (II), for the production of conjugates that can be used for the immunisation of donor animals and that lead ultimately to the production of monoclonal antibodies having a high degree of affinity towards said herbicide molecules.

The said sulfonamide moiety is preferably substituted arylsulfonyl, wherein the aryl radical is preferably a phenyl radical. Typical examples of sulfonylurea herbicides falling within the scope of formula (A) are described, for example, in EP 0 120 814.

In a preferred embodiment of the present invention, therefore, it is not the whole sulfonylurea molecule that is linked to the carrier molecule, but rather only a selected moiety thereof that comprises the particular desired determinant group in a form that is capable of triggering a very specific immune response. Especially preferred within the context of this invention is a fragment of the compound of formula (II) that remains restricted to the sulfonamide portion.

The said sulfonamide portion may be obtained, for example, by cleaving the corresponding sulfonylurea herbicide hydrolytically at the sulfonamide function using methods known per se. The sulfonamide linking fragment obtainable in that manner thus has a terminal —$SO_2$—$NH_2$ group to which it is then very easily possible to link a suitable bridge member which can be used for the subsequent conjugation of the hapten molecule. The linking of the bridge member can be achieved, for example, by reacting the previously mentioned —$SO_2$—$NH_2$ group with a reactive carboxylic acid derivative, such as a succinic acid derivative, or preferably with the corresponding anhydride. When a succinic acid derivative is used the group —$SO_2$—NH—C(O)—$CH_2CH_2$COOH is formed. The reaction is preferably carried out in a basic medium, especially in the presence of a suitable catalyst, such as the 1,8-diazabicyclo [5.4.0]undec-7-ene used in Example 1.1.

The fragment of the molecule according to the invention can of course also be prepared from known starting compounds and reactants by chemical synthesis.

The terminal carboxy grouping can also be convened using known methods that are frequently described in the literature into an amino group or an SH group that is likewise sufficiently reactive for linking the hapten molecule.

Suitable bridge members for the conjugation of the hapten to the carrier molecule are therefore especially compounds that contain at least one or more reactive groups that are capable of interacting with the freely accessible reactive groups of the carrier molecule.

Special preference is given within the context of this invention to the use of bridge members comprising from 2 to 10 bridge carbon atoms and having as reactive group(s) one or more reactive groups, such as amino, carboxy or SH group(s). Those reactive groups may be reacted using processes known per se with the reactive groups of the hapten molecule and the carrier molecule to form a hapten-carrier conjugate.

It is possible, for example, to bind a bridge member by way of a reactive amino group, using a dialdehyde (for example glutaraldehyde), to one of the free amino groups of the carrier molecule. If the bridge member has a reactive SH group, the conjugation of the hapten to the carrier molecule can be carried out by means of oxidation involving free SH groups of the carrier.

Special preference is given within the context of this invention to the use of bridge members having a carboxy group that can be linked with the aid of water-binding agents, such as a carbodiimide, preferably N,N'-dicyclohexylcarbodiimide, to a free amino group of the carrier molecule.

In order to link the antigen to the carrier protein, it is therefore advantageous first to produce a derivative capable of effecting that linking.

In a preferred embodiment of the present invention, for the preparation of conjugates that after immunisation of a donor animal lead to a specific immune response and ultimately to the production of monoclonal antibodies having a high degree of affinity towards sulfonylurea herbicides of formula (A), there is used a fragment that consists essentially of the sulfonamide moiety of the said sulfonylurea herbicide. After derivatising that fragment there is obtained a virtually ideal linking component that is outstandingly suitable for the production of monoclonal antibodies having a high degree of affinity towards sulfonylurea herbicides of formula (A).

Especially preferred are sulfonylurea derivatives of formula (III)

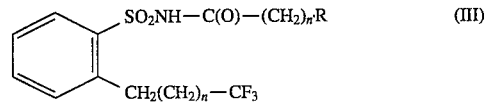

which can be thought of as being formed by replacement of the triazinamine grouping by an R'—$(CH_2)_{n'}$— group, and wherein R is COOH, $NH_2$ or SH, especially COOH;

n' is an integer from 1 to 10, preferably from 1 to 6; and n is an integer from 0 to 4, preferably 1, and which are therefore restricted to the sulfonamide portion.

Preference is given within the context of the present invention to a linking component wherein R is $NH_2$ and n' is an integer from 2 to 6, especially 3.

Special preference is given to a linking component wherein R is COOH and n' is an integer from 1 to 6, preferably 2.

Very special preference is given within the context of the present invention to the derivative of formula (IV)

$$\text{(IV)} \quad \underset{CH_2CH_2-CF_3}{\underset{|}{C_6H_4}}-SO_2NH-C(O)-CH_2-CH_2-COOH$$

which can be thought of as being formed by replacement of the triazinamine grouping by a —(CH$_2$)(CH$_2$)COOH grouping and which can be prepared in accordance with the process described in Example 1.1. The starting compounds and reactants that can be used in that process are known or can be prepared by analogy with known, structurally similar compounds.

Alternatively, for the production of monoclonal antibodies against sulfonylurea herbicides of formula (I), it is also possible to use a derivative according to formula (V) that can be prepared by derivatising the whole intact sulfonylurea molecule $$\text{(V)}$$

wherein

R$^1$, n and E are as defined for formula (I);

Y is an alkylene bridge having from 0 to 4 chain carbon atoms that may be interrupted beyond the C$_2$ position by oxygen and that is unsubstituted or mono- or polysubstituted by halogen or by C$_1$–C$_3$alkyl and that is bonded either directly or via sulfur or oxygen to the heterocyclyl carbon atom;

R' is COOH when m is an integer from 1 to 10, preferably from 1 to 6; and

R' is COOH, NH$_2$ or SH, but especially NH$_2$, when m is an integer from 2 to 10, preferably from 2 to 6.

Preference is given to a derivative according to formula (VI)

$$\text{(VI)}$$

having in the 4-position of the triazine ring an R"—(CH$_2$)$_m$—O— grouping wherein R" is COOH when m is an integer from 1 to 10, preferably from 1 to 6, and R" is COOH, NH$_2$ or SH, but especially NH$_2$, when m is an integer from 2 to 10, preferably from 2 to 6.

The resulting sulfonylurea derivatives that are capable of linking are novel and, by virtue of their specific linking ability, constitute a valuable starting material in the production of the monoclonal antibodies according to the invention. They therefore constitute an important part of the present invention.

According to the sulfonylurea derivative used, the actual linking reaction is preferably carried out using the active ester method or the diazonium method [Kelly et al (1985)]. When the active ester method is used, the sulfonylurea derivative is first solubilised in a suitable solvent. Suitable solvents are especially aprotic solvents that have a low evaporation rate, such as N,N-dimethylformamide (DMF) or dimethyl sulfoxide (DMSO).

The carboxy groups are then derivatised to form an active ester by reacting the previously solubilised sulfonylurea derivative with, for example, N-hydroxysuccinimide, N-hydroxysulfosuccinimide, N,N'-dicyclohexylcarbodiimide or N,N'-carbonyldiimidazole or with derivatives of those compounds.

The active ester is then separated off from the reaction mixture and added to BSA or KLH. After an incubation period of from 0.1 to 12 hours, preferably from 4 to 5 hours, the precipitate is removed. The supernatant can then be used for the actual immunisation reaction, if necessary after further purification steps.

In addition to the active ester method preferred within the context of this invention, it is also possible to use alternative methods for linking the hapten to the carrier molecule, for example the mixed anhydride method. In that method the carboxy group of the bridge member is linked to the carrier molecule using acetic anhydride or the carbodiimide derivative 1-ethyl-3-(3'-dimethylaminopropyl)carbodiimide.

If the linking of the derivative takes place by way of a reactive NH$_2$ group, it is preferable to use the diazonium method described by Kelly et al (1985).

In that method, sodium nitrite is added to the reactive NH$_2$ group in question, preferably at reduced temperature, especially at a temperature of approximately 0° C., in strongly acidic solution. The resulting diazonium salt is then added slowly to a buffered basic solution of the carrier molecule. That solution can then be used for the actual immunisation, if necessary after further purification steps.

The immunisation of the donor animals is effected by means of one or more administrations of the hapten linked to a high molecular weight carrier molecule. Special preference is given to 2 or 3 administrations, at intervals of from 7 to 30 days, especially from 12 to 16 days.

The form of administration preferred within the context of the present invention is injection, which may be effected intravenously, intraperitoneally or subcutaneously. A combination of subcutaneous and intraperitoneal injection is preferred.

The immunogen (sulfonylurea conjugate) is present in that case in a suitable buffer, for example a PBS buffer, that contains one of the adjuvants customarily used. Within the context of this invention special preference is given to the use of Freund's adjuvant.

After a rest period of from 0.5 to 4 months a further single administration ["boost"] of the hapten conjugate in a dose of from 10 µg to 1000 µg, especially from 50 µg to 5800 µg, is given.

Within a period of from 1 to 6 days after the final dose, the donor animals are sacrificed, the spleen is removed and a spleen cell suspension is prepared.

The isolated spleen cells are suspended in a suitable buffer (for example a BSS buffer) and stored in the form of a cell suspension until they are fused with suitable myeloma cells.

Those fusions were complicated originally by the fact that the myeloma cell lines also synthesised monoclonal antibodies, with the result that the hydrid produced two types of monoclonal antibodies: one originating from the myeloma cell and a second determined by the genetic information of the immunocompetent cell.

Within the context of the present invention, therefore, preference is given to the use of tumour cells that are not capable themselves of producing monoclonal antibodies, such as SP2/0-Ag14 (Shulman et al, 1978), X63-Ag8.653 or PAI [Stocker et al (1982)], which very much simplifies the analysis of the resulting fusion products. For successful fusion, it is advantageous for the spleen cells to be present in a 2 to 20 fold excess in relation to the myeloma cells.

The fusion of spleen and myeloma cells is carried out in a special fusion medium having a composition that provides optimum conditions for the intended cell fusion.

The said fusion medium is preferably a buffer solution that contains one of the fusion promotors customarily used for the fusion of cells, for example Sendai viruses or other paramyxoviruses, optionally in UV-inactivated form, calcium ions, surface-active lipids, for example lysolecithin or polyethylene glycol. Especially preferred within the context of this invention is the use of polyethylene glycol (PEG), especially polyethylene glycol (PEG) having an average molecular weight of from 600 to 6000, in a concentration of from 30% to 60%. Especially preferred is PEG 4000 at a concentration of approximately 50%. The optimum fusion temperature is from 18° C. to 39° C. Especially preferred is a temperature of 37° C.

Once the fusion of the immunocompetent spleen cells with the myeloma cells has taken place, the fused antibody-producing hybrid cells are selected using methods known per se.

Various possible methods exist for selecting successful fusion events (hybrid cells) from the two types of parent cells. Routinely, a million or more cells of each parent type are used in the fusion protocol. Since the fusion does not take place with 100% frequency, it can be difficult to separate the fusion products from the enormous number of non-fused parent cells and parent cells that have fused with themselves.

As already mentioned hereinbefore, the hybridoma cells are formed by fusion of short-lived antibody-producing (spleen) B cells with long-lived myeloma cells.

The desired result is a long-lived cell line that produces antibodies. Since the spleen cells have only a limited lifespan in culture, it is therefore possible in principle simply to wait until all the non-fused spleen cells and all the spleen cells that have fused with themselves have died. However, there then still remains the task of separating the long-lived anti-body-producing cells from the long-lived cells that do not produce antibodies.

A viable selection system is based on the availability or non-availability of the enzyme hypoxanthine-guanine phosphoribosyltransferase (HGPRT). That enzyme is a constituent of the purine salvage pathway in mammalian cells. Those cells are, moreover, also capable of synthesising purines de novo.

Under normal conditions the two methods of synthesis probably run parallel with one another to a certain extent.

If, however, a cell has no HGPRT, the salvage pathway is blocked and the purines have to be prepared from non-purine material.

For the selection of HGPRT-negative myeloma cells, there are generally used so-called purine antimetabolites, for example 8-azaguanine, which is structurally very similar to the purine guanine and can therefore replace the latter in some of its normal reactions.

Azaguanine is incorporated into DNA, which leads to impairment of normal growth behaviour and finally to the death of the cell. Since azaguanine has to be replaced by way of the salvage pathway, all the cells that have no HGPRT activity are unable to utilise azaguanine and therefore grow in its presence.

A selective system that operates with the same enzyme but in reverse, in that in this case HGPRT-positive cells are selected, is described in J. W. Littlefield (1964).

That selection system is based on the use of the so-called HAT medium which comprises, inter alia, hypoxanthine, aminopterin and thymidine (HAT medium) as constituents.

Aminopterin is an antimetabolite that inhibits de novo purine synthesis and the methylation of deoxyuridylate to form thymidylate.

Hypoxanthine is able to act as an auxiliary purine in the event of the aminopterin blocking the de novo purine synthesis, while thymidine renders superfluous the necessity for the methylation of deoxyuridylate.

Thus in the presence of aminopterin all HGPRT-positive cells proliferate, while the HGPRT-negative cells die.

In the hybrid system that is used for selection within the context of this invention, the myeloma cells are preferably resistant to azaguanine and sensitive to aminopterin, that is to say they am HGPRT-negative. The antibody-producing cells, on the other hand, are HGPRT-positive.

By fusing the cells and culturing them in a HAT medium, it is possible to select the cells that have successfully fused with one another, since the myeloma cells that are responsible for the proliferation are able to grow only in the presence of an HGPRT activity, and that activity has to be provided by the HGPRT-positive cell line.

Although the HGPRT-positive antibody-producing cell lines are not killed in that medium, they survive for only a certain period of time and are unable to proliferate.

Thus the fusion of the cells in a HAT medium creates a system in which the myeloma cells and the antibody-producing cells are able to grow for a period of time sufficient for the production of hybrid cells but in which only the hybrid cells are able to survive and proliferate.

In a special embodiment of the present invention the fused hybrid cells are cultured in the presence of macrophages, so-called feeder cells, previously isolated from the peritoneum of untreated, non-immunised experimental animals. For the culturing and selection of the fused hybrid cells, the cell suspension is divided into several aliquots and the individual aliquots are examined continuously for the development of hybrid cell cultures and for the formation of antibodies.

Especially preferred within the context of this invention is the culturing of the fused hybrid cells on microtitre plates.

The cell suspension obtained after fusion is divided amongst the individual wells in a microtitre plate and cultured for a period of from 7 to 30 days under conditions suitable for promoting the growth of the fused hybrid cells (for example HAT/HT media).

The supernatants of grown hybrid cultures are examined continuously for the formation of antibodies.

Positive hybrid cell cultures are then isolated by means of known methods, preferably using the limiting dilution method, and then cloned as pure cultures in suitable culture media.

The supernatants of the grown cell clones are likewise examined for the formation of antibodies.

The hybridoma cell clones according to the invention that have been produced in accordance with the foregoing description are preferably screened for the formation of suitable monoclonal antibodies using one of the immunoassays customarily used for that purpose, for example an enzyme-linked immunoassay or a radioimmunoassay.

In the enzyme-linked immunoassay the hapten conjugates characterised in detail hereinbefore are first adsorbed onto a solid carrier. The remaining free binding sites are then saturated, and thus blocked, by the addition of carrier molecules.

For the detection of monoclonal antibodies, aliquots of the supernatants of said hybridoma cell clones are incubated with the carrier-bound hapten conjugates.

The present invention relates also to the production of monoclonal antibodies using methods that are known per se, wherein the hybridoma cell lines according to the invention, characterised in detail hereinbefore, that synthesise the antibodies according to the invention and preferably secrete them into the surrounding medium, or clones or subclones thereof, are cultured in vitro or in vivo using known methods.

The in-vitro culturing of the hybridoma cells according to the invention is effected in suitable culture media, especially in the standard culture media customarily used, for example Dulbecco's Modified Eagle Medium (DMEM) or RPMI 1640 Medium, which may optionally be supplemented by the addition of mammalian sera, for example foetal calf serum, or by growth-promoting additives and trace elements.

The isolation of the monoclonal antibodies preferably begins with precipitation of the immunoglobulin fraction from the individual supernatants of the hybridoma cultures, for example using ammonium sulfate. There follow further working-up and purifying steps that are known to a person skilled in this field and that include, for example, the use of chromatographic methods, for example gel filtration, ion-exchange chromatography, DEAE-cellulose chromatography, protein A or immunoaffinity chromatography.

Large amounts of the monoclonal antibodies according to the invention may, however, also be obtained using in vivo methods.

For example, it is possible to inject into suitable mammals antibody-producing hybridoma cell clones that induce the development of antibody-producing tumours in the treated animals. After a period of from 1 to 3 weeks, the antibodies can be isolated from the body fluids of the animals so treated.

In a special embodiment of the present invention, female Balb/c mice that have optionally been pretreated with a hydrocarbon, such as pristane, are injected intraperitoneally with a hybridoma cell clone according to the invention.

From one to three weeks after the injection of the hybridoma cell clone, the ascites fluid is collected and stored until it is worked up further.

The isolation of the monoclonal antibodies is effected in a manner that is precisely analogous to the isolation described hereinbefore from the supernatants of hybridomas cultured in vitro.

The present invention relates also to the use of the antibodies according to the invention in one of the customary immunoassays for the detection of sulfonylurea herbicides of formula (A), especially for the detection of sulfonylurea herbicides of formula (I), and more especially for the detection of a compound of formula (II), and for the differentiation of the said sulfonylurea herbicides from structurally related compounds, such as triasulfurone, primisulfurone and chinosulfurone, and compound A in Table 2.

The monoclonal antibodies according to the invention can thus be used in all known immunoassays that are based on the specific binding between antigen and the corresponding monoclonal antibody, for example in a radioimmunoassay (RIA), an enzyme-linked immunoassay (ELISA), an immunofluorescence test, etc..

In an RIA test, the monoclonal antibody according to the invention can be used as such or in the form of a radioactively labelled derivative. All the modifications of RIA tests known hitherto can be used for the detection of the target substances relevant within the context of this invention, for example an RIA test in homogeneous or solid phase, a heterogeneous RIA test and a simple RIA test with direct or indirect (competitive) detection of the antigen. The same applies also to the use of an enzyme-linked immunoassay.

Preference is given within the context of this invention to the use of a monoclonal antibody according to the invention in a competitive immunoassay for the detection of sulfonylurea herbicides of formula (I), but especially for the detection of a compound of formula (II).

The principle of the competitive immunoassay is based on a competition between a labelled antigen or an antigen bound to a solid carrier and a free antigen for the relevant binding sites on the antibody molecule.

There are, in principle, two possible methods of carrying out that competitive immunoassay.

a) The first method is based on the competition between the antigen bound to a solid carrier and free antigen for the free binding sites on the antibody, which is provided with a marker. The binding of the antigen to a solid carrier can be effected either directly or by way of a carrier molecule.

The concentration of free antigen is determined in this case by means of the decrease in the labelled antibody bound to the carrier-fixed antigen. The decrease is proportional to the amount of free antigen contained in the sample.

b) An alternative method is based on the fact that free antigen and labelled antigen compete with one another for the relevant binding sites on the antibody, which in this case is bound to a solid carrier.

The concentration of free antigen is determined by means of the decrease in labelled antigen, which varies as a function of the concentration of free antigen.

Examples of solid carrier material suitable for binding the antigen or the antibody are the plastics surface of a microtitre plate or a test tube, the surface of beads of polystyrene, polypropylene, polyvinyl chloride, glass or plastics, or the surface of strips of filter paper, dextran cellulose or nitrocellulose, or similar materials. Those materials are coated with one of the monoclonal antibodies according to the invention or with an antigen, it being possible for the binding to the carrier material to be effected by simple adsorption or optionally after prior activation of the carrier material with, for example, glutaraldehyde or cyanogen bromide.

Special preference is given within the context of this invention to the use of the monoclonal antibody according to the invention in an enzyme-linked immunoassay [ELISA (enzyme linked immunosorbent assay)]. In such an immunoassay the monoclonal antibody according to the invention can be used as such or in the form of an enzyme-linked derivative.

An ELISA assay is based either on the use of an enzyme-linked derivative of the antibody according to the invention or on the use of enzyme-linked antibodies known per se that recognise an epitope of an antibody according to the invention and bind thereto.

Special preference is given within the context of this invention to the use of an ELISA assay in which one of the carrier materials described hereinbefore is first coated with an antigen. The carrier-bound antigen is then incubated with a test solution that contains the antigen to be detected and one of the antibodies according to the invention. The antigen to be detected may be present either in free form or as a constituent of a water or soil sample.

After an incubation period of from 10 minutes to 2 hours, the whole batch is incubated with an enzyme-labelled antibody that recognises the monoclonal antibody according to the invention and binds thereto. An example of such an enzyme-labelled antibody is a phosphatase-labelled goat anti-sheep immunoglobulin, or a corresponding goat anti-mouse antibody, which are commercially available.

The amount of bound antibody protein can be determined with the aid of an enzyme-substrate reaction, for example by means of spectroscopic methods.

Also preferred within the context of this invention is an ELISA test that is based on the competition between labelled and free antigen for the antibody bound to one of the carrier materials mentioned hereinbefore.

The amount of free antigen present in a specific sample is determined in this case by means of the decrease in labelled antigen, which is the more precise the more free antigen the sample contains.

The present invention relates further to means for the qualitative and quantitative determination of sulfonylurea herbicides of formula (A), especially for the determination of sulfonylurea herbicides of formula (I) and more especially for the determination of a compound of formula (II), in the form of a test kit that may comprise, in addition to the monoclonal antibodies according to the invention and/or their derivatives, optionally also other monoclonal or polyclonal antibodies, especially labelled monoclonal or polyclonal antibodies, and further additives.

Special preference is given within the context of this invention to test kits based on one of the immunoassays customarily used, selected from the group consisting of radioimmunoassay, enzyme-linked immunoassay and chemiluminescence assay. Especially preferred are test kits in which the detection of the target substance is based on a competitive immunoassay, especially on an enzyme-linked immunoassay (ELISA).

Test kits for the radioimmunological detection of a compound of formula (II) that are preferred within the context of this invention may comprise, for example, the following components:

(a) a suitable carrier material that may be uncoated or coated with one of the antibodies according to the invention or with an antigen conjugate;

(b) optionally freeze-dried or concentrated solutions of one of the antibodies according to the invention and/or of a radioactively labelled derivative thereof, or radioactively labelled antigen or standard solutions of the antigen;

(c) buffer solutions and (d) optionally polypeptides, detergents and other additives that, for example, prevent non-specific adsorption and aggregate formation and (e) pipettes, reaction vessels, calibration curves, packaging labels etc.

Test kits for the immunological detection of a compound of formula (II) that are based on an enzyme-linked immunoassay (ELISA) may comprise, for example, the following components:

(a) a suitable carrier material that may be uncoated or coated with one of the antibodies according to the invention or with an antigen conjugate;

(b) optionally freeze-dried or concentrated solutions of one of the antibodies according to the invention and/or of a second enzyme-labelled monoclonal or polyclonal antibody that is directed against the antigen to be determined or against an antibody that recognises the antigen;

(c) enzyme substrates in solid or dissolved form;

(e) the antigen or standard solutions of the antigen;

(f) buffer solutions;

(g) optionally polypeptides, detergents and further additives that, for example, prevent non-specific adsorption and aggregate formation and (h) pipettes, reaction vessels, calibration curves, colour charts, packaging labels, etc.

A test kit for the detection of a compound of formula (II) that is based on a chemiluminescence test may comprise, for example, the following components:

(a) a suitable carrier material that may be uncoated or coated with one of the antibodies according to the invention or with an antigen conjugate;

(b) optionally freeze-dried or concentrated solutions of one of the antibodies according to the invention and of a second polyclonal antibody that is capable of recognising the first antibody according to the invention and is linked to a chemiluminescent marker;

(c) solutions comprising a component that triggers the emission of light, for example $H_2O_2$ and NaOH; (d) buffer solutions; (e) optionally polypeptides, detergents and other additives that prevent non-specific adsorption and aggregate formation and (f) pipettes, reaction vessels, packaging labels, etc.

Carrier materials that may be used within the context of the present invention comprise especially insoluble, polymeric materials selected from the group consisting of polystyrene, polyethylene, polypropylene, polyester, polyacrylonitrile, polyvinyl chloride, polyacrylamide, nitrocellulose, cross-linked dextran, fluorinated resins, agarose, cross-linked agarose, polysaccharides, etc. It may also be possible, however, to use other materials, for example glass, metal, nylon-based netting, etc.

The carrier materials mentioned individually hereinbefore may be in very different forms and, depending on the specific intended use, may be in a wide variety of shapes. Those include, for example, dishes, beads, plates, small rods, cells, small bottles, small tubes, fibres, nets, etc.

Frequently used in the manufacture of test kits are, for example, microtitre plates made of transparent plastics materials, for example polyvinyl chloride or polystyrene, that may be uncoated or coated with one of the antibodies according to the invention, free antigen or an antigen conjugate. Also used are small beads, tubes or rods made of polystyrene and polystyrene latex, it being possible to separate the surrounding latex material from the polystyrene particles by means of centrifugation.

A further component of the test kit according to the invention are markers or indicators by means of which it is possible to detect the presence of a complex-forming reaction, especially an immune reaction, that preferably results in an antigen/antibody complex or in a ligand/receptor complex, it being possible in some cases to obtain quantitative as well as qualitative information regarding the antigen to be detected. Suitable markers or indicators are both individual atoms and molecules that may participate either directly or indirectly in the generation of a detectable signal. Those markers or indicators may be linked directly to the antigen to be detected or to one of the monoclonal antibodies according to the invention or may be incorporated therein. They may, however, alternatively be in the form of individual substances or in the form of a constituent of a separate compound that is neither the antigen to be detected itself nor one of the monoclonal antibodies according to the invention, but that is capable for its part of reacting with the receptor molecule, for example in the form of a complex formation.

Those separate compounds are preferably a second antibody molecule that may be of monoclonal or of polyclonal origin, a complement protein or fragments thereof, S.aureus protein A, etc. Those separate compounds recognise and bind specifically to a receptor molecule, for example the antigen to be detected or one of the monoclonal antibodies according to the invention, but preferably to a receptor molecule that is present in the form of a complex.

In many cases other, additional reagents are required that lead to a detectable signal only in cooperation with the marker. That is the case especially when enzymes are involved.

Markers or indicators that may be used within the context of the present invention are very well known to a person skilled in the art of immunology and immunochemistry. They include, for example, radioactively labelled elements or substances, enzymes or chemiluminescent substances. The following list of possible markers or indicators is intended merely to illustrate by way of example the great variety of the substances and reagents that may be used, without thereby limiting the subject of the invention in any way.

Suitable markers or indicators are to be found, for example, amongst the group of the radioactive elements. Preference is given especially to elements that either emit γ rays themselves, for example $^{124}I$, $^{125}I$, $^{128}I$, $^{132}I$, $^{51}Cr$, or that induce the emission of those rays, for example $^{11}C$, $^{18}F$, $^{13}N$. Also suitable are so-called β-emitters such as $^{111}In$, $^{14}C$ and $^{3}H$.

Further suitable markers include chemiluminescent substances, especially fluorescent substances, which can be very easily bound chemically to the antigen or an antibody without denaturing the antigen or the antibody. The resulting fluorochrome can be detected very easily by means of fluorometric methods. There may be mentioned individually here fluorochromes selected from the group consisting of fluorescein isocyanate, fluorescein isothiocyanate, 5-dimethylamino-1-naphthalenesulfonyl chloride, tetramethylrhodamine isothiocyanate, lissamine, rhodamine 8200 sulfonyl chloride, etc.

Other fluorescent agents and a description of analytical techniques are to be found in DeLuca, "Immunofluorescence Analysis", in: *Antibody As a Tool*, Marchalonis et al, John Wiley & Sons, Ltd., pp 189–231 (1982).

Special preference is given within the context of this invention to the use of enzymes as marker or indicator substances, for example horseradish peroxidase, alkaline phosphatase, β-D-galactosidase, glucose oxidase, glucoamylase, carboxylic acid anhydrase, acetylcholine esterase, lysozyme, malate dehydrogenase, glucose 6-phosphate dehydrogenase, etc. When using enzymes as marker substances it is necessary to add additional reagents that allow the formation of an immune complex to be monitored by way of the enzyme activity and optionally a stop reagent that can be used to terminate the enzyme reaction.

Special preference is given to reagents that lead to a colour reaction. In the case of horseradish peroxidase there may be mentioned by way of example hydrogen peroxide which, in conjunction with an additional, oxidised dyestuff precursor such as diaminobenzidine or o-phenylenediamine, leads to a brown or yellow colouring. When using glucose oxidase as marker substance it is possible, for example, to use 2,2'-azinodi(3-ethyl-benzthiazoline-6-sulfonic acid) [ABTS] as substrate.

The present invention therefore relates further to the use of test kits that comprise as reagent at least one of the monoclonal antibodies according to the invention for the rapid and effective, qualitative and/or quantitative detection of sulfonylurea herbicides of formula (A), especially for the detection of sulfonylurea herbicides of formula (I) and more especially for the detection of a compound of formula (II), and for the differentiation of those compounds from structurally related compounds, such as triasulfurone, primisulfurone and chinosulfurone, and compounds A and B in Table 2.

The monoclonal antibodies according to the invention may also be used to great advantage in so-called 'immunopurification' analyses, which are used especially in the analysis of residues. In those analyses, the antibodies according to the invention are bound covalently to a matrix, preferably a gel matrix, and then, in that bound form, are placed in a mini-column. That column can then be used for the purification of soil extracts.

The present invention therefore relates further to the use of one of the monoclonal antibodies according to the invention in an immunopurification process wherein (a) the said antibody is immobilised on a solid carrier;

(b) the said carrier is placed in a mini-column;

(c) a buffer solution comprising the sample to be purified or analysed is applied to the column;

(d) if necessary one or more washing steps are carried out; and (e) the analytes are eluted from the column using a suitable elution solution.

I. NON-LIMITING EXAMPLES

EXAMPLE 1

Preparation of the hapten/protein conjugate

Example 1.1: Preparation of 2-(3,3,3-trifluoropropyl-phenyl)-N,(1,4-dicarboxylic acid amide)-sulfonamide A derivative of a compound of formula (II) capable of linking to a carrier protein can be prepared in accordance with the following reaction scheme:

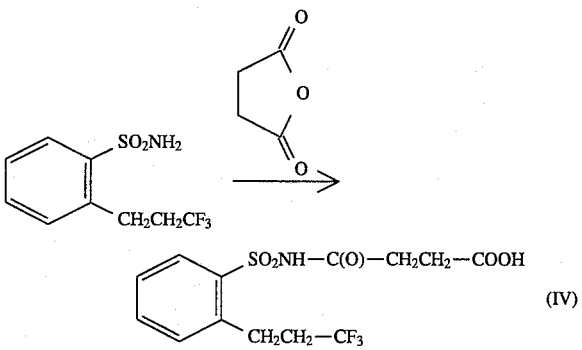

The individual steps of the method are as follows:

At room temperature, with slight cooling, 31.4 g of 1,8-diazabicyclo[5.4.0]undec-7-ene, dissolved in dioxane, are added dropwise over a period of half an hour to a solution of 25.3 g of 2-(3,3,3-trifluoropropyl)-phenylsulfonamide and 10.0 g of succinic acid anhydride in 250 ml of dioxane.

The resulting suspension is stirred for 15 hours at a temperature of from 20° to 25° C., acidified with 65 ml of 2N HCl, filtered and then dried. The product that precipitates is then purified on a silica gel column using toluene/ethyl acetate [3:1] as eluant, yielding 9.5 g of the title compound of formula (IV), which has a melting point of from 138° C. to 139° C.

The starting compounds and reactants used in the process described above are known or can be prepared analogously to known processes.

EXAMPLE 1.2

Hapten/protein conjugate

The derivative of the compound of formula (II) prepared in accordance with Example 1.1 is conjugated using the activated ester method (Kulkarni et al., 1981) either to bovine serum albumin (BSA; Fluka) or to keyhole limpet haemocyanin (KLH; Calbiochem).

1.2.1: Linking the compound of formula (IV) to BSH or KLH by the activated ester method In detail, the carboxy group of the compound of formula (IV) is solubilised at room temperature in N,N-dimethylformamide (DMF) (7.2 mg/200 μl) and then a 4 molar excess of N-hydroxysuccinimide (9.1 mg/200 μl) and N,N'-dicyclohexylcarbodiimide (16 mg/200 μl) is added thereto. The reaction mixture is stirred first for one hour at 22° C. and then for 18 hours at 4° C.

The precipitate formed during the reaction is removed by centrifuging at room temperature for 3 minutes at 12 000 g and the activated ester present in the clear supernatant is then added to BSA [12 mg] or KLH [12 mg] that has previously been solubilised in 3.3 ml of a phosphate-buffered salt solution (PBS-buffer).

After incubation for 4 hours at a temperature of 4° C., the precipitate that forms is removed by centrifuging at 4° C. for 10 minutes at 2 000 g and the supernatant, which contains the protein conjugate, is dialysed thoroughly against PBS before being used for the immunisation experiments.

The extent of the linking reaction is determined by absorption spectrophotometry. The molar ratio of hapten to BSA is approximately 20/1, preferably 23/1.

EXAMPLE 2

Immunisation

Two groups of 5 female, 4 to 6 week old BALB/c mice (Tierfarm Sisseln, Switzerland) receive a series of 3 intraperitoneal or subcutaneous injections of KLH conjugate at two-week intervals. The dosage for the conjugate prepared in Example 1.2.1 is 25 μg/injection.

The first injection contains 0.1 ml of the conjugate in PBS, which has been mixed in a ratio of 1:1 with 0.1 ml of complete Freund's adjuvant.

50 μl of that injection solution are injected intraperitoneally, and the remaining 150 μl subcutaneously.

In the second and third injections in the series, which take place 14 and 30 days, respectively, after the first administration, the complete Freund's adjuvant is replaced with incomplete Freund's adjuvant.

One week after the final injection, blood serum is taken from the experimental animals and the blood titre is determined by means of an ELISA test, the microtitre plates having previously been coated with BSA-conjugated hapten (see Section 6).

After a rest period of 2 months, a further single intraperitoneal injection of the KLH conjugates is given at a dosage of 220 μg/200 μl of PBS [hapten/protein conjugate]. From three to four days later the mice are sacrificed and the spleen cells isolated from them are fused with the myeloma cell line PAI [Stocker et al (1982)] [see Example 3.4].

EXAMPLE 3

Fusion protocol 3.1. Obtaining feeder cells (peritoneal macrophages).

Untreated Balb/c mice approximately six to eight weeks old are sacrificed one day before the intended fusion and sterilised by immersion in 70% alcohol.

The skin and the outer peritoneum are cut under sterile conditions without damaging the peritoneum. Using a sterile 5 ml plastics syringe and a sterile No. 18 injection needle, 4 ml of BSS (without $Ca^{2+}$ and $Mg^{2+}$) and 1 ml of air are injected into the abdominal cavity.

After light massage of the abdomen (syringe and needle remaining in the abdominal cavity), the previously injected BSS buffer is drawn off from the peritoneum and introduced into a sterile Falcon tube. This procedure is repeated twice. The macrophages so obtained are cooled with ice and then washed twice with 20 ml of BSS each time.

The macrophages are centrifuged for 10 minutes each time at 300 g and a temperature of 5° C. The pellet is then resuspended in 50 ml of HAT medium and the cell suspension is divided among 4 Costar plates having a total of 24 wells (0.5 ml/well).

The macrophages thus prepared are then stored in an incubator at a temperature of 37° C. and a $CO_2$ concentration of 6%.

Approximately $4 \times 10^6$ macrophages are required per fusion.

3.2. Culturing of the myeloma cell line PAI

The mentioned myeloma cell line PAI is a myeloma cell line that does not itself secrete any antibodies and that is described in Stocker et al. (1982).

50 ml of a well-grown culture comprising at least 10 million cells are required per fusion. The culturing of the myeloma cells is carried out preferably in T 175 Falcon bottles (Messrs. Beckton & Dickenson).

One day before the fusion the culture medium (RPMI 1640) is replaced with fresh RPMI 1640 medium. On the day of the fusion the PAI cells are harvested, introduced into a sterile 50 ml plastics tube and centrifuged for 10 minutes at 300 g and at a temperature of 5° C. (MSE centrifuge, Chilspin model, UK). After the centrifugation the supernatant is drawn off and discarded. The cells are washed twice with approximately 30 ml of BSS buffer (free of $Ca^{2+}$ and $Mg^{2+}$) each time (10 minutes at 300 g, 5° C.) and then resuspended in 5 ml of BSS.

An aliquot of the cell suspension is removed and stained with fluorescein diacetate (FDA) in order to determine the number of cells. The myeloma cells are stored on ice until they are used further.

3.3. Preparation of a spleen-cell suspension

The removal of the spleen from a Balb/c mouse previously immunised in accordance with Example 2 is effected under sterile conditions and while cooling with ice.

The previously immunised Balb/c mouse is sacrificed by breaking its neck and the spleen is removed under sterile conditions. For that purpose the mouse is immersed briefly in 70% ethanol and dissected using sterile instruments. The spleen is removed carefully and laid on a fine nylon net, where it is finely chopped using scissors and then pressed carefully through the net with the aid of a 5 ml syringe plunger without destroying too many cells in the process. During the entire operation the net is rinsed with BSS.

The cell suspension so obtained is introduced into 50 ml plastics tubes and centrifuged for 10 minutes at 300 g and at a temperature of 5° C. (MSE centrifuge, Chilspin model; UK). The cells are then washed twice with 20 ml of BSS each time (10 minutes; 300 g; 5° C.; MSE Chilspin) and after centrifugation the cell pellet is resuspended in 10 ml of BSS.

Until the fusion with PAI myeloma cells the spleen cells are kept on ice.

3.4. Fusion: spleen cells and PAI myeloma cells

The ratio of myeloma cells to spleen cells for the fusion should be 1:10.

Spleen cells (in BSS buffer) and PAI myeloma cells (in BSS buffer) are added together in the given ratio and centrifuged for 10 minutes at 300 g and at a temperature of 5° C. (MSE centrifuge, Chilspin model). The pellet is resuspended in BSS buffer and the suspension is then centrifuged again. The pellet is broken up by stirring carefully and placed in a water bath at 37° C. 1 ml of preheated sterile PEG-4000 (MERCK) is then added dropwise to the cells over a period of 60 seconds, the whole batch being agitated constantly. The cells are then shaken for a further 30 seconds before 5 ml of a previously heated BSS buffer (without $Ca^{2+}$, $Mg^{2+}$) are likewise added dropwise thereto over a period of approximately 5 minutes with constant stirring.

The cells fused in the manner described are then centrifuged down (10 minutes; 300 g; 20° C., MSE centrifuge, Chilspin model) and the supernatant is drawn off and discarded. The cell pellet is resuspended in 50 ml of HAT medium and the resulting cell suspension is divided among the 4 prepared Costar plates (microtitre plates having 24 wells, diameter per well 24 mm; total surface area for cell growth 2.0 $cm^2$) (0.5 ml/well).

The Costar plates are incubated at a temperature of 37° C. and at a $CO_2$ concentration of 6%.

EXAMPLE 4

Culturing the hybrid cells

On the first day after the cell fusion, 1 ml of HAT medium per well is added to the culture plates. 3 to 4 days after the cell fusion the fused cells are examined under a microscope. At the same time the spent medium is removed by suction and replaced with 1 ml of fresh HAT medium. After a further 3 days (6–7 days after the cell fusion) the culture medium is changed again. On the 7th to 10th day after the cell fusion each well is examined for hybrids under a microscrope and the medium is replaced from 2 to 3 times weekly.

As soon as hybrids have grown in a well, usually after 2 to 4 weeks, the HAT medium in that well can be replaced with HT medium. The supernatant of grown hybrid cultures (at least 10% of the well) is removed using a sterile Pasteur pipette and tested for the presence of antibodies.

As soon as a well is full of positive hybrid colonies, the latter can be transferred to new Costar plates in RPMI 1640 medium, the contents of a full well being divided among 2 or 3 new wells.

EXAMPLE 5

Cloning the positive hybrid cells

The cells in a positive well are detached with the aid of a pipette and transferred in 1 ml of medium into a tube. An aliquot is then removed and stained with FDA (dilution 1:2 with FDA: 50 µl cells +50 µl stain) in order to determine the number of cells. The preferred number of cells is from $10^5$ to $10^6$ cells/ml. The hybrid cells are then diluted with HT medium in a ratio of 1:100 (for example 100 µl of cells +9.9 ml of HT medium).

25 ml of HT medium are introduced into each of two 50 ml Falcon tubes and made up to a total of 30 ml per tube with 5 ml of a macrophage suspension. The macrophages have previously been isolated from a mouse and resuspended in 10 ml of HT medium (see Section 3.1).

In those Falcon tubes containing the macrophages the hybrid cells are diluted until a cell density of (i) 270 cells/30 ml and (ii) 90 cells/30 ml, respectively, has been reached. These batches are then divided among Costar plates (microtitre plates having 96 wells), 200 µl being introduced per well. This corresponds to a cell count of (i) 1.8 cells/well and (ii) 0.6 cell/well, respectively. 1.5 microtitre plates are thus required per dilution.

After 7 days the individual wells are examined under a microscope and the wells that contain cell clones are recorded. The dilution at which approximately 50% of the wells contain cell clones is used for the ELISA test. This should generally be a dilution of 0.6 cell/well. After approximately from 7 to 10 days the supernatants of the positive wells (with clones) are tested in an ELISA test for the presence of monoclonal antibodies and the positive clones are propagated on Costar plates (having 24 wells) in RPMI 1640 medium. Aliquots of those positive clones are stored in liquid nitrogen.

EXAMPLE 6

Hybridoma screening (ELISA test)

First of all 100 µl of a solution of BSA-conjugated hapten [2 µg/ml] in sodium carbonate buffer (50mM, pH 9.6) are introduced into the individual wells in a microtitre plate and the batch is incubated overnight at 4° C. in a humidity chamber. Each of the wells is then washed five times with a 0.1% PBS Tween buffer. In order to block the unoccupied binding sites on the microtitre plate, 200 µl of a PBS-BSA solution (1%) are introduced into each well. The batch is incubated for 1–2 hours at room temperature and then washed with a 0.1% PBS Tween buffer.

200 µl of the hybridoma supernatant diluted in a ratio of 1:2 with PBS Tween (0.1%) are then introduced into each well and the whole batch is incubated for 2 hours at room temperature. The wells are then washed again five times with a 0.1% PBS Tween buffer.

There follows incubation with phosphatase-conjugated goat anti-mouse antibody (Kirkegaard & Perry Lab.). There are first added to each well 100 µl of a goat antibody to mouse IgG, purified by affinity chromatography, that is present in a 1:1500 dilution in PBS Tween (0.1%) (Kirkegaard & Perry Laboratories) and is labelled with alkaline phosphatase.

The incubation period is 1.5 hours at room temperature. The individual wells are then washed again with PBS Tween (0.1%) (five times).

150 µl of a substrate-containing solution (1 mg/ml of p-nitrophenyl phosphate) are then introduced into each well. After an incubation period of 2 hours in the dark, spectroscopic determination is carried out at 405 nm. Positive hybridoma cells that secrete a specific antibody emit a strong positive signal at the chosen wavelength. Those cells are then cloned using the limiting dilution method [Godings (1980)]. Pure monoclonal antibodies can be obtained from the ascites fluid of suitably pretreated mice [Campbell AM, (1984)]

EXAMPLE 7

Expansion of hybridoma cells in the mouse

In order to stimulate the production of ascites, female Balb/c mice (20–25 mg) (Tierfarm Sisseln, CH) are pretreated with 0.3 ml of pristane oil (Aldrich Chemical) which is injected intraperitoneally. From 1 to 3 weeks after the administration of pristane, the mice receive a second injection (0.2 ml of pristane oil, i.p.). At the same time as this second injection the animals receive $2\times10^6$ hybridoma cells in 0.2 ml of PBS.

The ascites fluid resulting from that treatment is collected, centrifuged at 800 g and stored at a temperature of −20° C. After thawing, the ascites fluid is centrifuged for 1 hour at 30 000 g. The topmost layer, which comprises predominantly lipids, is removed. The protein concentration is then determined and adjusted to a value of 10 mg/ml by the addition of PBS.

The immunoglobulin G fraction (IgG) is precipitated by the dropwise addition of 0.9 part by volume of a saturated ammonium sulfate solution at 0° C. After 1 hour the IgG fraction is pelleted by centrifugation for one hour at 22 000 g. The pellet is then dissolved in 20 mM tris-HCl buffer, pH 7.9, containing 50 mM NaCl, and dialysed against the same buffer overnight at 4° C. Further working up of the IgG fraction is carried out by means of anion-exchange chromatography on a DE-52 diethylaminoethylcellulose (Whatmann) column. The sample is diluted 1:2 (v/v) with 20 mM tris-HCl, pH 7.9, until a final NaCl concentration of 25mM has been reached, and 10 mg of protein/ml of gel are applied to the column. Elution is achieved by increasing the NaCl concentration from 25 mM to 200 mM (linear gradient). In general, the elution of monoclonal antibodies takes place in the region of 80 mM NaCl.

The fractions are dialysed against PBS overnight at a temperature of 4° C. and stored at −70° C. The degree of purity is determined by means of sodium dodecylsulfate polyacrylamide gel electrophoresis (SDS-PAGE), and by isoelectric focusing.

In the present case the degree of purity is >90%.

EXAMPLE 8

Detection of a compound of formula (II)

The detection of a compound of formula (II) can be effected by means of a two-step competitive ELISA test.

BSA-conjugated hapten, prepared in accordance with Example 1.2.1, in a 50 mM sodium carbonate buffer (pH 9.6) (200 ng of BSA-conjugated hapten/100 µl of 50 mM sodium carbonate buffer) is first of all adsorbed on microtitre plates (for example Dynatech, type M 129A) and incubated overnight at a temperature of 4° C.

The plates are then washed five times with PBS buffer enriched with 0.1% (v/v) polysorbate 20 (Tween 20) (PBS Tween).

The remaining free binding sites of the solid carrier material are then blocked by the addition of PBS-BSA in the form of a 1% (w/v) solution. After incubation for two hours at 22° C. the plates are washed again with PBS Tween (0.1%).

50 µl of the supernatant of the previously cloned hybridoma cells (in a dilution of from 1:1000 to 1:2000) or 50 µl of the previously purified monoclonal antibodies (40– 120 ng/ml) are incubated a) with 950 µl of a standard solution containing an increasing amount of antigen [compound of formula (II)] or of antigen analog, b) with antigen-containing water samples or c) with antigen-containing soil extracts. [All dilutions are carried out in PBS Tween (0.1%)].

After an incubation period of 1 hour at room temperature (22° C.), 200 µl of the antigen/antibody mixture are added to each well in the microtitre plate and the whole batch is incubated for a further one hour. The wells are then washed five times with PBS Tween (0.1%) and charged with 100 µl/well of goat anti-mouse IgG antibody that is conjugated to alkaline phosphatase (dilution 1:1500), and incubated for a period of 1.5 hours.

After washing again, 150 µl/well of the substrate p-nitrophenyl phosphate dissolved in 1 mg/ml of diethanolamine buffer (1 mM, pH 9.8, enriched with 0.5 mM $MgCl_2 \times 6H_2O$) are added to the wells.

After an incubation period of 2 hours at a temperature of 22° C., a colour change is observed that is proportional to the amount of antibody that has reacted with the antigen bound to the solid phase. The intensity of the colour reaction that has occurred is determined at a wavelength of 405 nm. The dilutions of the individual samples are so chosen that without the addition of an inhibitor (Bo) absorption values in a range of from 0.3 to 0.5 are obtained. For the controls (without antibody) values of $A_{405}<0.01$ are obtained. All the samples are determined in triplicate.

In order to determine the amount of antigen [compound of formula (II)] present in a sample, first of all a calibration curve is produced, B/Bo×100 being plotted against the concentration of inhibitor. (Bo represents the absorption capacity measured without the addition of an antigen inhibitor to the antibody, and B is the absorption capacity when antigen inhibitors at various concentrations are added). The $I_{50}$ value indicates the concentration of the antigen at which the binding of antibody to the solid phase is inhibited by 50%. The $I_{50}$ value is determined using an ENZFITTER (Leatherbarrow, Elsevier-Biosoft) curve-calculation program based on a four-parameter logistical curve (Raab GM, 1983) and specially adapted to the prevailing conditions. The quantitative determination of antigen in soil or water samples within the context of ELISA is also carried out using the ENZFITTER program, the adaptation of the curve being based on standards that run on any microtitre plate.

EXAMPLE 8.1: Analysis of soil samples

Aliquots (2 g) of standard soil samples of different origins are extracted in accordance with the methods described below:

Method (A) [according to Iwanzik and Egli (1989)]: A 100 g sample is extracted for 2 hours in an extractor by shaking with 300 ml of a 2:1 mixture (v/v) of methanol and an aqueous phosphate buffer (PB) [pH 7.0, total phosphate concentration 0.07M]. After filtering and acidifying with phosphoric acid, the sulfonylurea compound is re-extracted 3 times with 75 ml of $CH_2Cl_2$. After evaporating off the solvent, the sample is dissolved in 10 ml of PB buffer and purified by means of filtration.

Method (B): The extraction according to method (A) is repeated with two further samples and the last organic phase is purified further by shaking with an aqueous hydrogen carbonate solution (5%) [Iwanzik and Egli (1989)]. After the addition of tetrabutylammonium hydrogen carbonate, the sulfonylurea compound is re-extracted in dichloromethane/n-hexane (80:20). After evaporating off the organic phase, the sulfonylurea compound is taken up in 10 ml of PB buffer. Before the sample is used in the ELISA test, it is diluted in PBS Tween 0.1% in a ratio of 1:20 or 1:40.

Method (C): In this case the extraction by shaking is effected using tetrabutylammonium hydroxide directly with the methanol/PB extract. The aqueous phase is then transferred to a liquid-liquid partitioning cartridge [ClinElut® No. 1010, Analytichem International, Harbor City, Calif.] and washed with 30 ml of n-hexane. The sulfonylurea compound is eluted with dichloromethane/n-hexane (60:40). The organic phase is evaporated and the residue that remains is taken up in PBS.

Example 8.2: Analysis of water samples

For competitive ELISA, 100 µl of PBS Tween buffer in a tenfold concentration are added to 850 µl of a water sample. The batch is then incubated with 50 µl of the antibody.

EXAMPLE 9

Immunopurification

The monoclonal antibodies produced in accordance with Example 7 are immobilised on a solid carrier, preferably a Sepharose 4B gel activated by cyanogen bromide [CN—Br]. The latter is then packed into a minicolumn routinely used in purification processes.

Before the soil sample to be analysed is applied, the column is conditioned by washing with from 5 to 10 ml of PBS buffer [pH 7.4].

The aqueous soil sample extract is taken up in 50 ml of buffer solution and applied dropwise to the column. The column is then washed one or more times with 20 ml of a washing solution consisting of water or a 9:1 mixture of water and acetonitrile.

The elution of the analytes is effected by the addition of an acetonitrile elution solution which is preferably enriched with 5% of a phosphorous acid. The efficiency of that elution process increases as the flow rate of the eluate decreases. A flow rate of <0.5% is ideal.

II. RESULTS

1) Production of monoclonal antibodies (a) Starting from 4 fusion events using mice that have been immunised with the KLH conjugate prepared in accordance with Example 1.2.1, a hybridoma is obtained that produces a monoclonal antibody having a high degree of affinity towards a compound of formula (II) [MAb 4197-70-12]. The fusion efficiency is approximately 90%.

The cross-reactivities with the compounds of Table 1 found for that MAb are below 0.1%. Especially remarkable is the fact that the said MAb exhibits no cross-reactivity with triasulfuron, which is structurally very closely related.

The lower detection limit for the target compound [compound of formula (II)] using the MAb according to the invention (in buffer) is in the region of 0.1 ng/ml of buffer. The corresponding $I_{50}$ value for MAb 4197-70-12 is 0.8 ng/ml.

III DEPOSIT

The hybridoma cell line prepared and used within the context of the present invention was deposited on 6th Dec., 1991 under deposit number ECACC 911 20619 with the 'European Collection of Animal Cell Cultures' (ECACC) in Salisbury, UK, a recognised international depository, in accordance with the requirements and regulations of the Budapest Treaty on the International Recognition of the Deposit of Microorganisms for the Purposes of Patent Procedure. A declaration of the viability of the deposited samples is issued by the said international depository.

| Cell line | Date of deposit | Deposit number | Date of certificate of viability |
|---|---|---|---|
| hybridoma clone 4197-70-12 | 06.12.1991 | 911 20619 | 06.12.1991 |

IV. MEDIA AND BUFFERS (A) RPMI 1640 medium

RPMI 1640 (Seromed) with the following additives:

| calf serum | 15% |
|---|---|
| L-glutamine | 4 mM |
| gentamycin | 0.01% |
| sodium pyruvate | 1 mM |
| 2-mercaptoethanol | 50 µM |
| insulin | 5 µM |
| transferrin | 5 µM |
| selenium (ITS) | 5 µM |

(B) HAT medium 1 liter of RPMI 1640 medium with 20 ml addition of HAT conc. (50×) from Boehringer, having the following composition:

| hypoxanthine 680 | 5.0 mg/l |
|---|---|
| aminopterin | 8.8 mg/l |
| thymidine | 193.8 mg/l |

(C) HT medium 1 liter of RPMI 1640 medium with 20 ml addition of HT conc. (50×) from Boehringer, having the following composition:

| hypoxanthine 680 | 5.0 mg/l |
|---|---|
| thymidine | 193.8 mg/l |

(D) BSS buffer [Earle's salt solution, without Ca and Mg, pH 7.4]

| KCl | 7.3 mM |
|---|---|
| NaCl | 116.0 mM |
| NaHCO$_3$ | 26.0 mM |
| NaH$_2$PO$_4$.2H$_2$O | 1.0 mM |
| glucose | 5.5 mM |
| phenol red | 48.0 µM |

1% (v/v) addition of a penicillin/streptomycin solution (Seromed) [10 000 U penicillin, 10 mg/ml streptomycin]

(E) Sodium carbonate buffer [pH 9.6]

| Na$_2$CO$_3$ | 477.0 mg |
|---|---|
| NaHCO$_3$ | 879.0 mg |
| NaN$_3$ | 1.8 mg |
| ad 300 ml H$_2$O | |

(F) PBS buffer [pH 7.0]

| NaCl | 8.5 g |
|---|---|
| Na$_2$HPO$_4$.2H$_2$O | 1.28 g |
| NaH$_2$PO$_4$.2H$_2$O | 0.436 g |
| ad 1000 ml H$_2$O | |

(G) PBS TWEEN 20 [0.1%]

1 ml Tween 20 (Serva)+1000 ml PBS (H) PBS BSA [1%]

| BSA | 5.0 g |
|---|---|
| NaN$_3$ (0.5M) | 3.0 ml |
| ad 500 ml PBS | |

(I) Substrate buffer [diethanolamine buffer, pH 9.8]

| | |
|---|---|
| diethanolamine | 97.0 ml |
| $NaN_3$ (0.5M) | 6.0 ml |
| $MgCl_2.6H_2O$ | 100.0 mg |
| ad 1000 ml $H_2O$, adjustment of the pH to 9.8 with conc. HCl | |

Preparation of the substrate: immediately before use a substrate tablet (=5 mg) of the p-nitrophenyl phosphate substrate (Sigma 104) is dissolved in 5 ml of substrate buffer.

V. BIBLIOGRAPHY

Ahmad I. and Crawford G., *J. Agric. Food Chem.*, 38: 138–141, 1990

Campbell A. M., "Monoclonal Antibody Technology", in: *Laboratory Techniques in Biochemistry and Molecular Biology*; Burdon, R. H.; Knippenberg P. H. (Eds.); Elsevier: Amsterdam, 1984; Vol. 13, pp. 120–184

DeLuca, "Immunofluorescence Analysis", in: *Antibody As a Tool*, Marchalonis et al, John Wiley & Sons, Ltd., pp 189–231 (1982)

Ercegovich C. D. et al, *J. Agric. Food Chem.*, 29: 559–563, 1981

Feng et al, *J. Agric. Food Chem.*, 38: 159–163, 1990

Fleeker J., *J. Assoc. Off. Anal. Chem.*, 70: 874–878, 1987

Hargrave H. S. and Merkle M. G., *Weed Sci.*, 19: 1971

Iwanzik W. et al, *Z. PflKrankh. PflSchutz, Suppl. XI*: 301–310, 1988

Kawamura H., Berzojsky J. A., *J. Immunol.*, 136: 58, 1986

Kelley M. et al, *J. Agric. Food Chem.*, 33: 962–965, 1985

Köhler G., Milstein, *Nature*, 256: 495–497, 1975

Kulkarni N. P. et al, *Cancer Res.*, 41: 2700–2706, 1981

Littlefield J. W., *Science*, 145: 709, 1964

Newsome W. H., *J. Agric. Food Chem.*, 33: 528–530, 1985

Raab G. M., *Clin. Chem.*, 29: 1757–1761, 1983

Schlaeppi J. -M. et al, *J. Agric. Food Chem.*, 37: 1532–1538, 1989

Shulman M. et al, *Nature*, 276: 269–270, 1978

Stocker J. W. et al, *Hoffmann-La Roche Research Disclosure*, 21713: 155–157, 1982 van Rensburg E., *Analyst*, 110: 733., 1985

Wie S. I., Hammock B. D., *J. Agric. Food Chem.*, 30: 949–957, 1982

Zahnow E. W., *J. Agric. Food Chem.*, 30: 854–857, 1982

Patent literature

EP-0 120 814

VI. TABLES

TABLE 1

Cross-reactivities of various analogs of the compound of formula (II)

| | MAb 4197-70-12 | |
|---|---|---|
| Compound | (a) I 50 (ng/ml) | (b) cross-reactivity (%) |
| Compound of formula (II) | 0.8 | 100 |
| A | >1000 | <0.1 |
| B | >1000 | <0.1 |
| C | >1000 | <0.1 |
| D | >1000 | <0.1 | a) Inhibitor concentration that reduces the ELISA signal by 50% in comparison with the control.
b) (antigen conc. for 50% inhibition/concentration of the antigen analog for 50% inhibition) × 100.

The analogs of the compound of formula (II) A to D are shown below with the aid of their structural formulae.

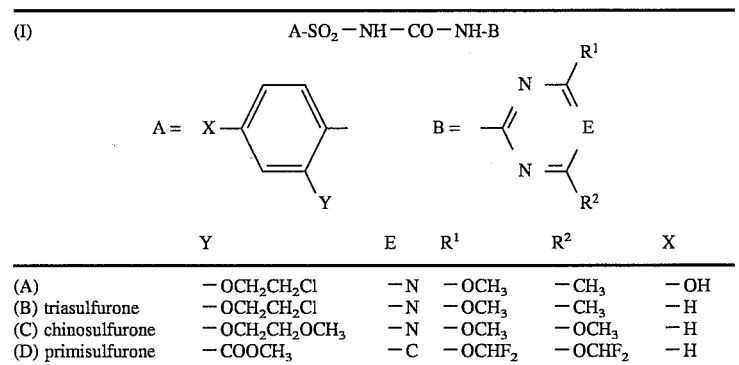

| | Y | E | $R^1$ | $R^2$ | X |
|---|---|---|---|---|---|
| (A) | $-OCH_2CH_2Cl$ | $-N$ | $-OCH_3$ | $-CH_3$ | $-OH$ |
| (B) triasulfurone | $-OCH_2CH_2Cl$ | $-N$ | $-OCH_3$ | $-CH_3$ | $-H$ |
| (C) chinosulfurone | $-OCH_2CH_2OCH_3$ | $-N$ | $-OCH_3$ | $-OCH_3$ | $-H$ |
| (D) primisulfurone | $-COOCH_3$ | $-C$ | $-OCHF_2$ | $-OCHF_2$ | $-H$ |

What is claimed is:

1. A linking component of formula (III)

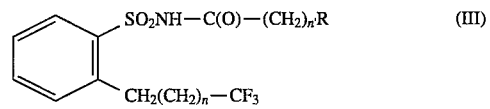

wherein

R is COOH, $NH_2$ or SH; and n' is an integer from 1 to 10; and n is an integer from 0 to 4.

2. A linking component according to claim 1, wherein R is $NH_2$ and n' is an integer from 2 to 6.

3. A linking component according to claim 1, wherein R is $NH_2$ and n'=3.

4. A linking component according to claim 1, wherein R is COOH and n' is an integer from 1 to 6.

5. A linking component according to claim 4, wherein R is COOH and n'=2.

6. A linking component according to claim 1, wherein n=1.

* * * * *